US009706927B2

United States Patent
Edwards et al.

(10) Patent No.: US 9,706,927 B2
(45) Date of Patent: Jul. 18, 2017

(54) MOBILE REFLECTANCE OPTICAL SPECTROSCOPY DEVICE AND PROCESS OF USING AND ASSEMBLING MOBILE REFLECTANCE OPTICAL SPECTROSCOPY DEVICE

(71) Applicant: ATOPTIX, LLC, State College, PA (US)

(72) Inventors: Perry S. Edwards, State College, PA (US); Zhiwen Liu, State College, PA (US)

(73) Assignee: Atoptix, LLC, State College, PA (US)

( * ) Notice: Subject to any disclaimer, the term of this patent is extended or adjusted under 35 U.S.C. 154(b) by 162 days.

(21) Appl. No.: 14/684,638

(22) Filed: Apr. 13, 2015

(65) Prior Publication Data

US 2016/0296118 A1    Oct. 13, 2016

(51) Int. Cl.
*A61B 5/00* (2006.01)
*G01J 3/18* (2006.01)
*G01J 3/02* (2006.01)
*G01J 3/42* (2006.01)

(52) U.S. Cl.
CPC .......... *A61B 5/0075* (2013.01); *A61B 5/6801* (2013.01); *A61B 5/6898* (2013.01); *A61B 5/742* (2013.01); *G01J 3/0229* (2013.01); *G01J 3/0272* (2013.01); *G01J 3/18* (2013.01); *G01J 3/42* (2013.01); *A61B 2562/12* (2013.01); *G01J 2003/425* (2013.01)

(58) Field of Classification Search
CPC ... A61B 5/0075; A61B 5/6801; A61B 5/6898; A61B 5/742; A61B 2562/12; G01J 3/0229; G01J 3/0272; G01J 3/18; G01J 3/42; G01J 2003/425

USPC ........................................................ 356/326
See application file for complete search history.

(56) References Cited

U.S. PATENT DOCUMENTS

| 5,461,475 A * | 10/1995 | Lerner | G01J 3/28 356/300 |
| 5,706,083 A * | 1/1998 | Iida | G01J 3/02 356/328 |
| 6,480,273 B1 * | 11/2002 | Brock | G01J 3/28 356/300 |
| 8,861,086 B2 | 10/2014 | Liu et al. | |
| 2010/0051802 A1 * | 3/2010 | Marchman | H01J 37/226 250/306 |

(Continued)

*Primary Examiner* — Kara E Geisel
*Assistant Examiner* — Hina F Ayub
(74) *Attorney, Agent, or Firm* — McNees Wallace & Nurick LLC

(57) ABSTRACT

Devices for reflectance spectroscopy, processes of assembling devices for reflectance spectroscopy, and health care processes of using reflectance optical spectroscopy devices are disclosed. The devices include a light source arranged and disposed to apply broadband light to sample, and a light-receiving feature configured to receive reflected light produced by the applying of the broadband light to the sample. The light-receiving feature is arranged and disposed to direct the reflected light to an optical detection system and isolate the reflected light from the broadband light. The optical detection system is capable of differentiating individual frequencies of the reflected light. The processes of assembling include removably positioning the devices on electronic devices. The health care processes include positioning the devices.

20 Claims, 2 Drawing Sheets

(56) References Cited

U.S. PATENT DOCUMENTS

| | | | |
|---|---|---|---|
| 2012/0038918 A1* | 2/2012 | Liu | B29D 11/00269 |
| | | | 356/328 |
| 2014/0131578 A1* | 5/2014 | Hruska | G01N 21/359 |
| | | | 250/339.02 |
| 2015/0109427 A1* | 4/2015 | Wood | A61B 1/043 |
| | | | 348/68 |
| 2015/0156394 A1* | 6/2015 | Denis | H04N 5/23212 |
| | | | 348/349 |
| 2016/0123869 A1* | 5/2016 | Messerschmidt | A61B 5/0075 |
| | | | 356/39 |
| 2016/0249810 A1* | 9/2016 | Darty | A61B 5/0075 |
| | | | 600/477 |

\* cited by examiner

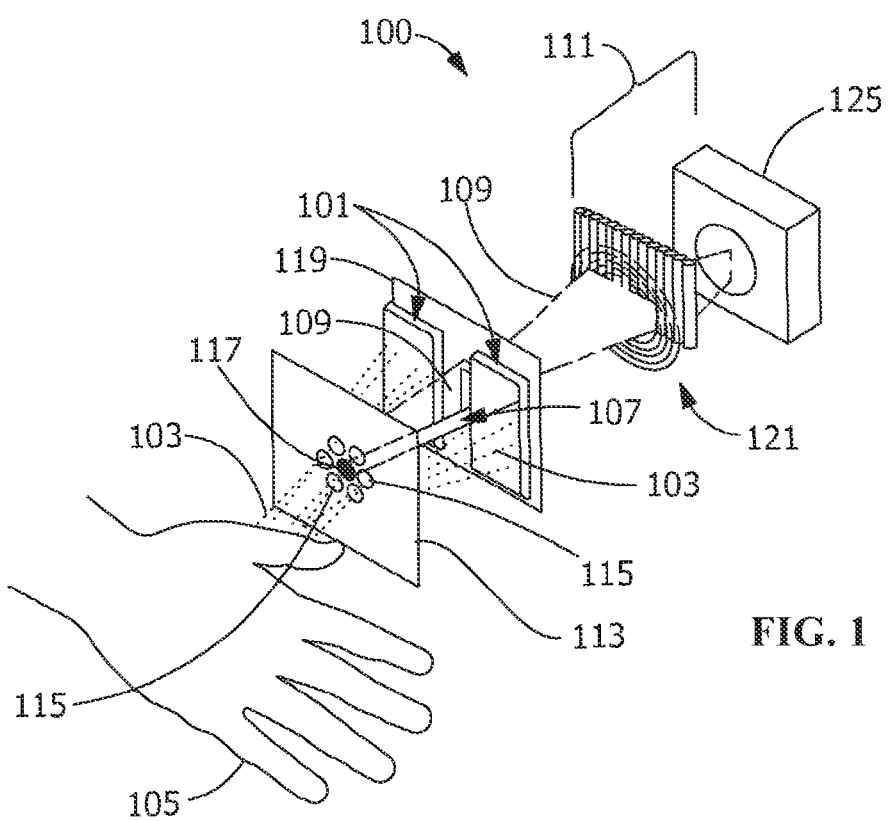
FIG. 1
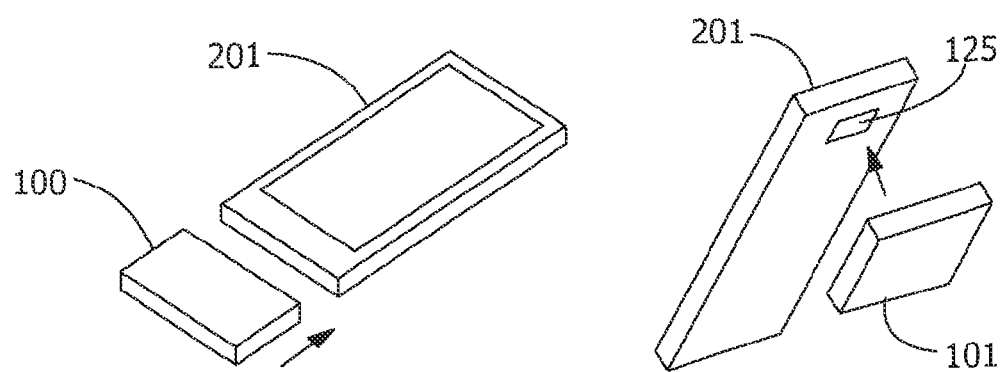
FIG. 2
FIG. 3

MOBILE REFLECTANCE OPTICAL SPECTROSCOPY DEVICE AND PROCESS OF USING AND ASSEMBLING MOBILE REFLECTANCE OPTICAL SPECTROSCOPY DEVICE

FIELD OF THE INVENTION

The present invention is directed to optical spectroscopy. More particularly, the present invention is directed to reflectance optical spectroscopic devices, assembly of reflectance optical spectroscopic devices, and processes of using reflectance optical spectroscopic devices.

BACKGROUND OF THE INVENTION

Characterization of the vital properties of tissue (for example, concentrations of deoxy- and oxy-hemoglobin, melanin, scattering coefficient) is important for personal wellness monitoring as well as diagnosis of diseases and complications. For example, anemia, polycythemia, and other diseases call for frequent hemoglobin testing and monitoring. According to the World Health Organization (WHO), anemia affects nearly 2 billion people or roughly 30% of the world's population. For women, menometrorrhagia, or extended bleeding from the uterus, is one of the more frequent reasons that doctors send patients to the lab for hemoglobin test. Diabetics can suffer from reduced feeling and loss of awareness of reduced circulation in extremities, which can lead to the development of diabetic lesions as well as other skin diseases, and in some severe cases, amputation.

Existing technology has limited capability to provide sufficiently low-cost, rapid/real-time, effective, and noninvasive means for clinicians and patients to measure and track such conditions. For example, extremity circulation, which can alert to the possible development of conditions (for example, ischemia) before they occur and monitor them during treatment is not sufficiently monitored and tracked, while meeting each of these needs. Likewise, tissue vitals (for example, hemoglobin level and oxygen saturation) are not sufficiently capable of being monitored and tracked, while meeting each of these needs. In contrast, tests to monitor such conditions are usually performed in a hospital lab or clinical facility, requiring significant infrastructure and resources, not accessible in remote regions, resource-scarce communities, or financially struggling communities.

A reflectance optical spectroscopy device, assembly of reflectance optical spectroscopy device, and a process of using a reflectance optical spectroscopy device that show one or more improvements in comparison to the prior art would be desirable in the art.

BRIEF DESCRIPTION OF THE INVENTION

In an embodiment, a device for reflectance optical spectroscopy includes a light source arranged and disposed to apply broadband light to sample, and a light-receiving feature configured to receive reflected light produced by the applying of the broadband light to the sample. The light-receiving feature is arranged and disposed to direct the reflected light to an optical detection system and isolate the reflected light from the broadband light. The optical detection system is capable of differentiating individual wavelengths of the reflected light.

In another embodiment, a process of assembling a device for spectroscopy includes removably positioning a mobile device on an electronic device. The mobile device includes a light source arranged and disposed to apply source light to a sample, and a light-receiving feature configured to receive light produced by the applying of the source light to the sample. The light-receiving feature is arranged and disposed to direct the light to an optical detection system and isolate the light from the source light. The optical detection system is capable of differentiating individual wavelengths of the light.

In another embodiment, a health care process using reflectance optical spectroscopy includes positioning a spectroscopic device, the spectroscopic device including a light source arranged and disposed to apply broadband light to a sample, a light-receiving feature configured to receive reflected light produced by the applying of the broadband light to the sample. The light-receiving feature is arranged and disposed to direct the reflected light to an optical detection system and isolate the reflected light from the broadband light. The optical detection system is capable of differentiating individual wavelengths of the reflected light.

Other features and advantages of the present invention will be apparent from the following more detailed description, taken in conjunction with the accompanying drawings which illustrate, by way of example, the principles of the invention.

BRIEF DESCRIPTION OF THE DRAWINGS

FIG. 1 is a schematic view of an embodiment of a reflectance optical spectroscopy device having a mask, according to the disclosure.

FIG. 2 is a perspective view of an embodiment of a reflectance optical spectroscopy device capable of being secured to a mobile device in a parallel orientation, according to the disclosure.

FIG. 3 is a perspective view of an embodiment of a reflectance optical spectroscopy device capable of being secured to a mobile device in a non-parallel orientation, according to the disclosure.

Wherever possible, the same reference numbers will be used throughout the drawings to represent the same parts.

DETAILED DESCRIPTION OF THE INVENTION

Figure 4:
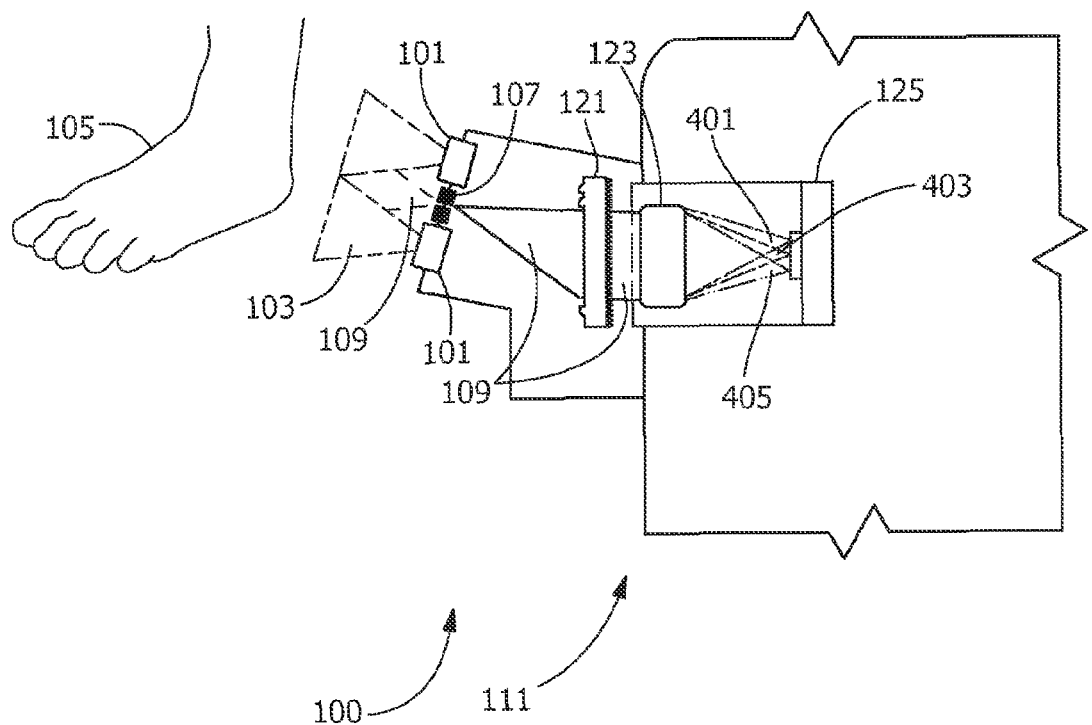
FIG. 4 is a schematic view of an embodiment of a reflectance optical spectroscopy device having a lens assembly that utilizes built-in detecting systems, specifically, a camera, on an electronic device, according to the disclosure.

Provided are reflectance optical spectroscopy devices, assembly of reflectance optical spectroscopy devices, and processes of using reflectance optical spectroscopy devices. Embodiments of the present disclosure, for example, in comparison to concepts failing to include one or more of the features disclosed herein, permit characterization of vital properties of tissue (for example, concentrations of deoxy- and oxy-hemoglobin, melanin, scattering coefficient), permit monitoring of tissue vitals (for example, hemoglobin level and oxygen saturation), permit low-cost monitoring of certain conditions, permit rapid/real-time monitoring of certain conditions, permit non-invasive monitoring of certain conditions, permit reduction or elimination of consequential injuries/illness/death, permit conditions to be monitored in remote regions (for example, without infrastructure and resources), permit other suitable advantages and distinctions that will be apparent from the disclosure, and/or permit a combination thereof.

FIG. 1 depicts an embodiment of a spectroscopic device 100 for reflectance spectroscopy, such as diffuse reflectance spectroscopy. The spectroscopic device 100 includes a light source 101 arranged and disposed to apply broadband light 103 to a sample 105, such as, tissue, for example, on or below a human hand, a human forearm, a human foot, skin tissue, any other suitable surface capable of being analyzed by reflectance spectroscopy, or a combination thereof. Other suitable surfaces include, but are not limited to, cellulosic surfaces, for example, external plant surfaces, such as, leaves, roots, stalks, and/or bark, and/or internal plant materials, such as, pith, xylem, cambium, and/or phloem. Yet other suitable surfaces include, but are not limited to, food, such as, meats, cheeses, fruits, vegetables, and/or beverages. Even further suitable surfaces include, pharmaceutical surfaces (for example, drug coatings and/or active pharmaceutical ingredients), industrial surfaces (for example, industrial coatings, chemical compositions, metals or metallics, and/or polymeric materials), and/or by-products (for example, waste streams, environmental materials, and/or oil/gas constituents).

The light source 101 provides a combination of light in the wavelength of ultraviolet light, visible light, and near infrared light. For example, as used herein, the term "broad band light" includes wavelengths within the ultraviolet spectrum, the visible spectrum, and the near infrared spectrum. In further embodiments, the broadband light is or includes a range of between 300 nanometers to 1,000 nanometers, between 450 nanometers and 900 nanometers, between 300 nanometers and 800 nanometers, 700 nanometers and 1,700 nanometers, 900 nanometers and 2.5 micrometers, or any suitable combination, sub-combination, range, or sub-range therein.

The light source 101 for producing the broadband light 103 is any suitable device capable of producing the selected range of wavelength. Suitable devices include, but are not limited to, light emitting diodes, lasers, lamps, or combinations thereof.

Upon the broadband light 103 being applied to the sample 105, diffuse reflected light 109 is produced. In one embodiment, the diffuse reflected light 109 is at least partially segregated/isolated from the broadband light 103, for example, by a mask plate 113. The mask plate 113 includes any arrangement for facilitating the segregation/isolation of the diffuse reflected light 109 and the broadband light 103. One suitable configuration includes an array of illuminating apertures 115 configured for receiving the broadband light 103 and extending around one or more detection apertures 117 configured for receiving the diffuse reflected light 109. In this embodiment, during operation of the spectroscopic device 100, the broadband light 103 extends through the mask plate 113 in a direction away from the light source 101 and the diffuse reflected light 109 extends through the mask plate 113 in an opposite direction toward the light source 101 and then a light-receiving feature 107.

In one embodiment, the mask plate 113 includes the detection aperture(s) 117 being positioned with the illuminating apertures 115 in a ring surrounding the detecting aperture(s) 117, the center-to-center distances between each of the illuminating apertures 115 and the detecting aperture(s) 117 being identical. Suitable center-to-center distances include, but are not limited to, between 400 micrometers and 800 micrometers, between 500 micrometers and 1 millimeter, between 1 millimeter and 5 millimeters, between 5 millimeters and 1 centimeter, between 1 centimeter and 10 centimeters, or any suitable combination, sub-combination, range, or sub-range therein.

The detection aperture(s) 117 and the illuminating apertures 115 are produced through any suitable techniques permitting the segregation of the corresponding light. In one embodiment, the detection aperture(s) 117 and/or the illuminating apertures 115 are produced by direct machining on a metal or metallic plate, to produce the mask plate 113. In another embodiment, the detection aperture(s) 117 and/or the illuminating apertures 115 are produced by photolithography, for example, to define a chromium mask on a quarts or glass substrate, thereby producing the mask plate 113. In a further embodiment, the mask plate 113 produced by the photolithography includes transmission of greater than 80%, 85%, 90%, or any suitable combination, sub-combination, range, or sub-range therein, in regions without chromium. Additionally or alternatively, in a further embodiment, the mask plate 113 produced by the photolithography includes an attenuation optical density of greater than 1, greater than 3, or any other suitable value in regions with it.

In general, the light-receiving feature 107 is positioned to receive the diffuse reflected light 109. The light-receiving feature 107 is arranged and disposed to direct the diffuse reflected light 109 to an optical detection system 111 and isolate the diffuse reflected light 109 from the broadband light 103. The light-receiving feature 107 is any suitable mechanism or arrangement. Suitable mechanisms include, but are not limited to, an aperture or slit within a substrate 119, a wave guide (such as fiber-optics), a reflected-light collection sub-system (for example, patterned using a mask), or a combination thereof.

The optical detection system 111 is capable of differentiating individual wavelengths of the diffuse reflected light 109, for example, by use of spectrometers, filters, and/or any other suitable wavelength-selective device. In one embodiment, the optical detection system 111 includes an optical element 121 (for example, a transmission G-Fresnel optical element, as described in U.S. Pat. No. 8,861,086, issued Oct. 14, 2014 and titled "COMPACT SPECTROMETER INCLUDING A DIFFRACTIVE OPTICAL ELEMENT WITH DUAL DISPERSION AND FOCUSING FUNCTIONALITY", the entirety of which is incorporated by reference) and/or a lens assembly 123, as shown in FIG. 4, positioned to receive the diffuse reflected light 109.

Upon travelling through the optical element 121 and/or the lens assembly 123, wavelengths are separated, for example, to a first wavelength 401, a second wavelength 403, and a third wavelength 405, as shown in FIG. 4. The wavelengths are within the diffuse reflected light 109 and are separated and/or become capable of differentiation, thereby being sensed and/or captured by a detector 125 (for example, a camera sensor or camera detector). In one embodiment, the wavelengths to be differentiated include, but are not limited to, a range between 300 nanometers to 1,000 nanometers, between 450 nanometers and 900 nanometers, between 300 nanometers and 800 nanometers, 700 nanometers and 1,700 nanometers, 900 nanometers and 2.5 micrometers, or any suitable combination, sub-combination, range, or sub-range therein.

In one embodiment, the light source system 101 includes a modulator, for example, configured for spatial and/or temporal modulation of the illumination light 103. In one embodiment, the optical detection system 111 comprises a system for detecting one or both of spatial and temporal modulation of the diffuse reflected light 109.

In one embodiment, the optical detection system 111 includes a monochromator or a spectrometer, for example, a Czerny-Turner monochromator/spectrometer or a Fastie-Ebert monochromator/spectrometer.

Referring to FIGS. 2-3, in one embodiment, the spectroscopic device 100 is modular and capable of being connected and removably positioned relative to an electronic device 201 (for example, a wired, wireless device, and/or mobile device), such as, a cellular telephone, a notebook, a laptop computer, a bench top instrument, or any other device capable of being used in a variety of environments. Referring to FIG. 2, in one embodiment, the spectroscopic device 100 secures to and/or couples with the electronic device 201 in a parallel or substantially parallel orientation. Referring to FIG. 3, in another embodiment, the spectroscopic device 100 secures to and/or couples with the electronic device 201 in a non-parallel orientation, such as, perpendicularly, at an angle of between ninety degrees and zero degrees, at an angle between ten degrees and fifty degrees, at an angle of between 40 degrees and 80 degrees, or any suitable combination, sub-combination, range, or sub-range therein. In one embodiment, the spectroscopic device 100 is standalone and capable of communicating with an electronic device. In one embodiment, the spectroscopic device 100 is a wearable device and, for example, is capable of being worn on fingers, hands, feet, waist, or a combination thereof.

Upon being secured and/or coupled to the electronic device 201, the spectroscopic device 100 is powered by the electronic device 201 or is powered separately from the electronic device 201 (for example, by a battery). Likewise, upon being secured and/or coupled to the electronic device 201, the spectroscopic device 100 communicates with the electronic device 201 (for example, by sending data or executing operations in response to commands from the electronic device 201) or operates without communicating with the electronic device 201 (for example, by operating autonomously). Operational connection of the spectroscopic device 100 and the electronic device 201 is through any suitable technique, such as, using a USB connector, using an IOS connector, using wireless IR connection, using Bluetooth, using wireless RF connection, using other suitable techniques, or a combination thereof.

Figure 5:
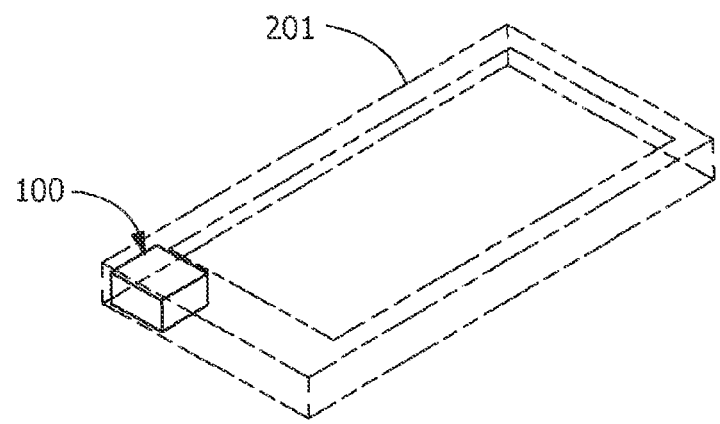
FIG. 5 is a schematic perspective view of an embodiment of a reflectance optical spectroscopy device integral within a wireless device, according to the disclosure.

Referring to FIG. 5, according to one embodiment, the spectroscopic device 100 is a self-contained and non-modular device including (for example, in a concealed manner) the light source 101, the mask plate 113, the illuminating apertures 115, the detection aperture(s) 117, the light-receiving feature 107, and the optical detection system 111.

In one embodiment, the spectroscopic device 100 is used in health care processes, for example, therapeutic and/or diagnostic procedures. In such processes, a medical professional, a technician (skilled or unskilled), a patient, or another individual positions the spectroscopic device 100, thereby enabling the spectroscopic device 100 to operate and gather information and/or data. Such techniques are capable of being performed in remote regions without infrastructure, such as hospitals, and/or can operate in conjunction with systems operably connected through the internet, satellite, or other transmission systems.

In one embodiment, the spectroscopic device 100 automatically or based upon input commands from the operator controls operation of the light source 101 and/or the optical detection system 111. For example, in one embodiment, the electronic device 201 drives the light source 101 and provides full control of the light source 101, for example, through an electronics control board (not shown) in the spectroscopic device 100 interfacing with the electronic device 201 that is controlled by a microprocessor system on the electronics control board, for example, by adjusting output power.

In one embodiment, such control permits the camera detector 125 to adjust exposure time, for example, from 1 millisecond to 100 milliseconds, from 100 milliseconds to 1 second, from 1 second to 60 seconds, from 1 minute to 10 minutes, or any suitable combination, sub-combination, range, or sub-range therein. Additionally or alternatively, in some embodiments, such control permits the focusing features of the camera detector 125 to fine tune alignment.

The spectroscopic device 100 includes any other suitable operational features. For example, in one embodiment, the spectroscopic device 100 includes temperature-control features responsive to stabilize temperatures of the spectroscopic device 100, the broadband light 103, and/or the surface of the sample 105 to temperatures suitable for measurements. For example, in one embodiment, the spectroscopic device 100 includes pressure-control features responsive to control pressure values associated with the contact.

While the invention has been described with reference to one or more embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In addition, all numerical values identified in the detailed description shall be interpreted as though the precise and approximate values are both expressly identified.

What is claimed is:

1. A device for reflectance spectroscopy, comprising:
    a light source arranged and disposed to apply broadband light to a sample;
    a light-receiving feature configured to receive reflected light produced by the applying of the broadband light to the sample;
    a system for selectively facilitating spatial segregation of the reflected light from the broadband light, the system having a plurality of passage ways for delivering the broadband light to the sample, the broadband passage ways positioned around and spatially separated from at least one passage way for receiving the reflected light, the broadband light and the reflected light passing through the system in opposite directions;
    wherein the light-receiving feature is arranged and disposed to direct the reflected light to an optical detection system and isolate the reflected light from the broadband light; and
    wherein the optical detection system is capable of differentiating individual wavelengths of the reflected light.

2. The device according to claim 1, wherein the light source includes light emitting diodes.

3. The device according to claim 1, wherein the light source includes one or both of a laser and a lamp.

4. The device according to claim 1, wherein the light-receiving feature is or includes an aperture within a substrate.

5. The device according to claim 1, wherein the light-receiving feature is or includes a wave guide.

6. The device according to claim 1, comprising a mask plate, wherein the broadband light extends through the mask plate in a direction away from the light source and the reflected light extends through the mask plate in an opposite direction toward the light source and the light-receiving feature.

7. The device according to claim 1, wherein the device is modular and capable of being connected and removed from an electronic device.

8. The device according to claim 7, wherein the electronic device is a cellular telephone.

9. The device according to claim 7, wherein the device secures to the electronic device in a parallel or substantially parallel orientation.

10. The device according to claim 7, wherein the device secures to the electronic device in a non-parallel orientation.

11. The device according to claim 7, wherein the electronic device controls the function of the device and display information on a built-in display screen of the electronic device.

12. The device according to claim 1, wherein the device is integrated within an electronic device.

13. The device according to claim 1, wherein the device is wearable and communicates wirelessly with an electronic device.

14. The device according to claim 1, wherein the optical detection system comprises a system for detecting one or both of spatial and temporal modulation.

15. The device according to claim 1, wherein the light source is within a light source system, the light source system comprising a modulator for one or both of spatial and temporal modulation.

16. The device according to claim 1, wherein the optical detection system comprises a spectrometer.

17. The device according to claim 1, wherein the optical detection system comprises a G-Fresnel optical element positioned between the light-receiving feature and an image detector.

18. The device according to claim 1, wherein the optical detection system comprises a plurality of filters for differentiating individual wavelengths of the light.

19. A process of assembling a device for spectroscopy, the process comprising:
removably positioning a mobile device on an electronic device,
wherein the mobile device includes a light source arranged and disposed to apply source light to a sample, and a light-receiving feature configured to receive reflected light produced by the applying of the source light to the sample;
removably positioning a system to selectively, spatially segregate the reflected light from the source light, the system having a plurality of passage ways for delivering the source light to the sample, the source light passage ways positioned around and spatially separated from at least one passage way for receiving the reflected light, the source light and the reflected light passing through the system in opposite directions;
wherein the light-receiving feature is arranged and disposed to direct the reflected light to an optical detection system and to isolate the reflected light from the source light;
wherein the optical detection system is capable of differentiating individual wavelengths of the light.

20. A health care process using reflectance spectroscopy, the process comprising:
positioning a spectroscopic device, the spectroscopic device including a light source arranged and disposed to apply broadband light to a sample, a light-receiving feature configured to receive reflected light produced by the applying of the broadband light to the sample;
positioning a system to selectively, spatially segregate the reflected light from the broadband light, the system having a plurality of passage ways for delivering the broadband light to the sample, the broadband passage ways positioned around and spatially separated from at least one passage way for receiving the reflected light, the broadband light and the reflected light passing through the system in opposite directions;
wherein the light-receiving feature is arranged and disposed to direct the reflected light to an optical detection system and isolate the reflected light from the broadband light; and
wherein the optical detection system is capable of differentiating individual wavelengths of the reflected light.

* * * * *